US010123705B2

(12) United States Patent
Alfano et al.

(10) Patent No.: US 10,123,705 B2
(45) Date of Patent: Nov. 13, 2018

(54) DEEP OPTICAL IMAGING OF TISSUE WITH LESS SCATTERING IN THE SECOND, THIRD AND FOURTH NIR SPECTRAL WINDOWS USING SUPERCONTINUUM AND OTHER LASER COHERENT LIGHT SOURCES

(71) Applicant: Robert R. Alfano, Bronx, NY (US)

(72) Inventors: Robert R. Alfano, Bronx, NY (US); Laura Sordillo, New York, NY (US); Yang Pu, New York, NY (US); Lingyan Shi, New York, NY (US)

( * ) Notice: Subject to any disclaimer, the term of this patent is extended or adjusted under 35 U.S.C. 154(b) by 79 days.

(21) Appl. No.: 15/243,165

(22) Filed: Aug. 22, 2016

(65) Prior Publication Data

US 2017/0049326 A1    Feb. 23, 2017

Related U.S. Application Data

(60) Provisional application No. 62/283,107, filed on Aug. 21, 2015.

(51) Int. Cl.
*A61B 5/00* (2006.01)
*A61C 19/04* (2006.01)
(Continued)

(52) U.S. Cl.
CPC .......... *A61B 5/0075* (2013.01); *A61B 5/0086* (2013.01); *A61C 19/041* (2013.01); *G01N 21/359* (2013.01); *G01N 21/4795* (2013.01); *A61B 5/0088* (2013.01); *A61B 5/0091* (2013.01); *A61B 5/02007* (2013.01); *A61B 5/4504* (2013.01); *A61B 2090/3614* (2016.02); *A61B 2562/0238* (2013.01)

(58) Field of Classification Search
None
See application file for complete search history.

(56) References Cited

U.S. PATENT DOCUMENTS

| | | | | |
|---|---|---|---|---|
| 4,945,239 A | * | 7/1990 | Wist .................... | A61B 5/0091 250/339.02 |
| 2007/0027362 A1 | * | 2/2007 | Handa ................ | A61B 1/00009 600/160 |

OTHER PUBLICATIONS

M. Cutler, "Transillumination as an aid in the diagnosis of breast lesions," Surg. Gynecol. Obstet. 48, 721-729 (1929).

(Continued)

*Primary Examiner* — Edwin Gunberg
(74) *Attorney, Agent, or Firm* — Myron Greenspan Lackenbach Siegel LLP

(57) ABSTRACT

Coherent light is used to image cells/molecules at wavelengths in the near-infrared (NIR) region in second, third and fourth spectral windows. Optical attenuation from thin tissue slices of normal and malignant breast and prostate tissue, and pig brain are placed between matched bandpass filters, within desired windows and measured within an NIR spectral window at wavelengths selected to highlight the desired cells/molecules. Due to a reduction in scattering and minimal absorption, longer attenuation and clearer images can be seen in the second, third and fourth NIR windows compared to the conventional first NIR window. The spectral windows have uses in microscope imaging one or more collagens, elastins, lipids and carotenoids in arteries, bones, breast, cells, skin, intestines, bones, cracks, teeth, and blood due to less scattering of light and improved signal to noise to provide clearer images.

17 Claims, 11 Drawing Sheets

(51) Int. Cl.
*G01N 21/359* (2014.01)
*G01N 21/47* (2006.01)
*A61B 90/00* (2016.01)
*A61B 5/02* (2006.01)

(56) References Cited

OTHER PUBLICATIONS

B. Chance, E. Anday, S. Nioka, S. Zhou, H. Long, K. Worden, C. Li, T. Turray, Y. Ovetsky, D. Pidikiti, and R. Thomas, "A novel method for fast imaging of brain function, non-invasively, with light," Optics Express 2, 411-423 (1998).

L. Wang, P. P. Ho, and R. R. Alfano, "Time-resolved Fourier spectrum and imaging in highly scattering media," Appl. Opt. 32, 5043-5048 (1993).

R. R. Anderson, and J. A. Parrish, "The optics of human skin," J. Invest. Dermatol. 77, 13-19 (1981).

\* cited by examiner

Fig. 2(a)
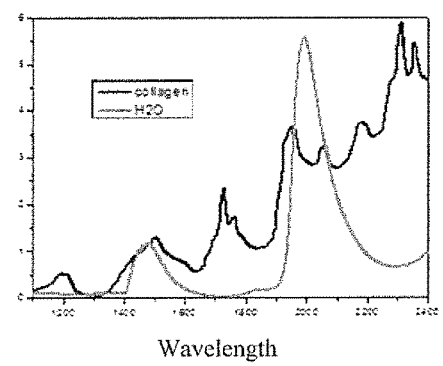
Wavelength
Fig. 2(b)
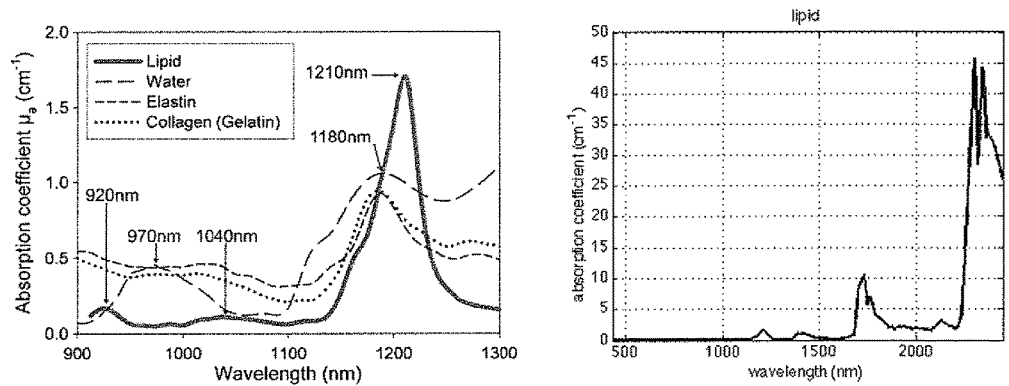
Fig. 2(c)

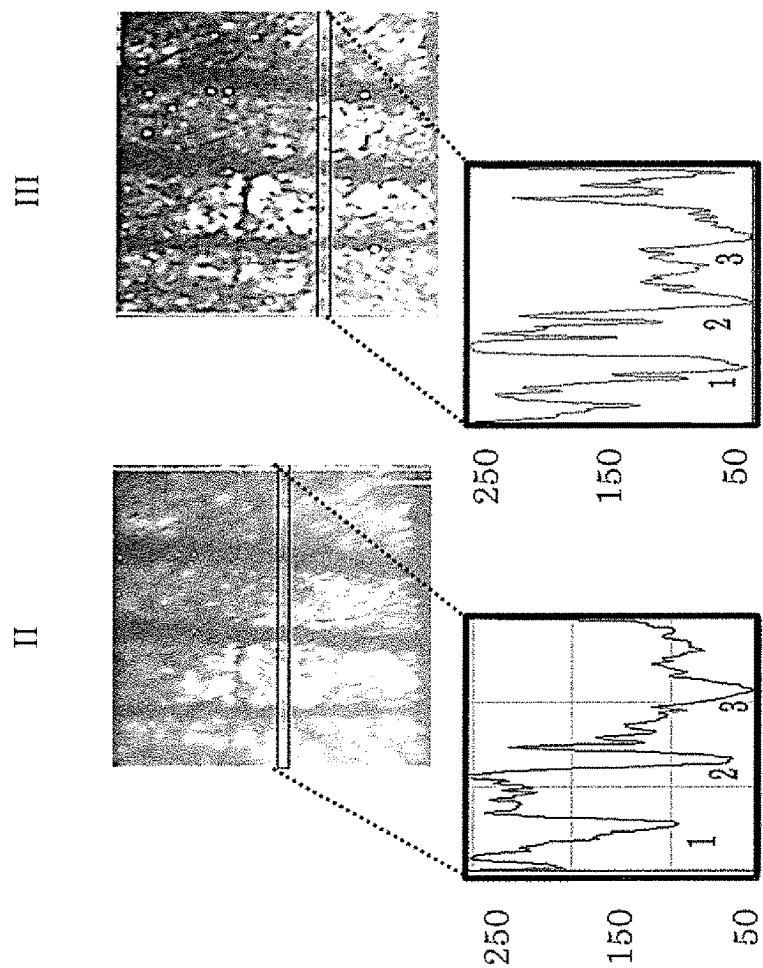

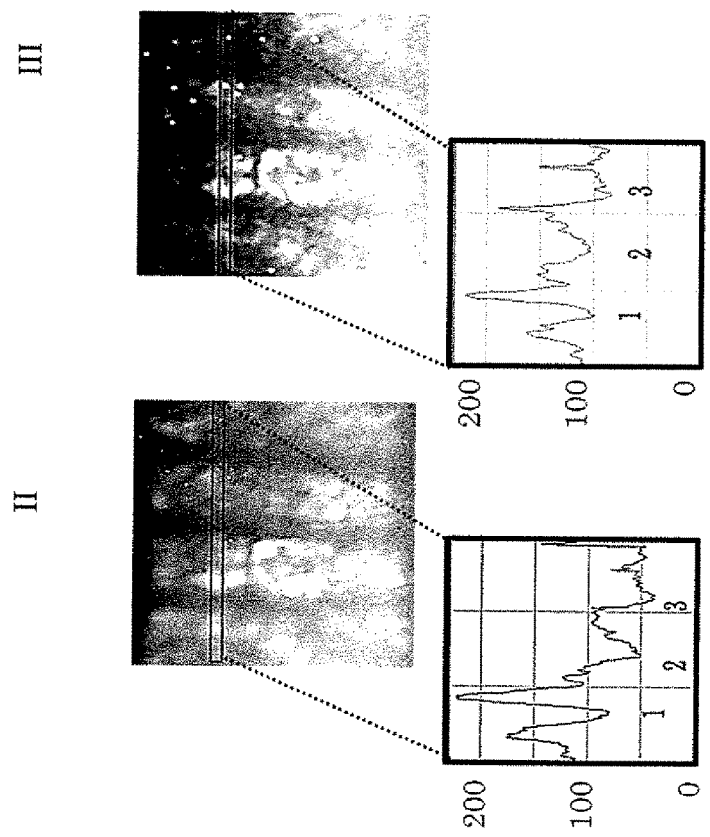

DEEP OPTICAL IMAGING OF TISSUE WITH LESS SCATTERING IN THE SECOND, THIRD AND FOURTH NIR SPECTRAL WINDOWS USING SUPERCONTINUUM AND OTHER LASER COHERENT LIGHT SOURCES

BACKGROUND OF THE INVENTION

1. Field of the Invention

The invention generally relates to optical imaging of tissue and, more specifically, to second, third and fourth near-infrared spectral windows for deep optical imaging of tissue with less scattering.

2. Description of Prior Art

It is well known that light at wavelengths in the visible to near-infrared (NIR) range from 650 nm to 950 nm is a non-invasive optical tool to detect and image tissue abnormalities with Silicon based detectors. Optical mammography, for example, is an alternative NIR technique which utilizes NIR light to identify and image cancerous breast lesions. NIR light allows for greater depth penetration, minimal absorption and scattering into tissue than at shorter wavelengths in the visible region. The tissue becomes clearer in NIR region>900 nm. By choosing the appropriate wavelength of light and CCD detector, one can increase the penetration depth into tissue media and produce clearer optical images into NIR such as InGaAs and InSb detectors.

In 1929, Dr. Culter reported using white light and optical transillumination to image the breast [1]. He had hoped to replace to use of X-rays with longer wavelengths of light in the visible and NIR, however, due to lack of appropriate detectors and laser sources, he was unsuccessful. Since that time, better detectors, laser sources, and computer technologies have allowed others, such as B. Chance and R. R. Alfano, to use frequency modulation and time resolved imaging, respectively, to effectively image breast abnormalities [2, 3]. Nowadays, the NIR region with wavelengths from 650 nm to 950 nm, called the first therapeutic window, is conventionally used for most NIR tissue imaging studies and photodynamic therapy applications [4]. This NIR optical window shows less scattering and minimal absorption than in the visible range due to the inverse wavelength n>1 power dependence. At longer wavelengths, less scattering and blurring of optical images will occur. Just as the first optical window shows less scattering than in the visible range, it is expected that longer NIR wavelengths of light, above 950 nm, show less scattering and higher contrast images than the first optical window into >1000 nm.

BRIEF DESCRIPTION OF DRAWINGS

The above and other aspects, features and advantages of the present invention will be more apparent from the following description when taken in conjunction with the accompanying drawings, in which:

FIGS. 2(a)-2(c) are NIR absorption spectra of (a) collagen, (b) lipids and elastin and (c) a combination of vibrational modes, respectively;

FIGS. 8(a)-8(d) are transmission images of chicken tissue with thicknesses (a) no top layer, (b) 1.6 mm, (c) 2.8 mm, and (d) 3.9 mm, respectively, covering three black wires of different depths with corresponding spatial intensity distribution spectra using the second (II) and third (III) optical windows.

DESCRIPTION OF THE INVENTION

1. Introduction

The patent teaches longer NIR wavelengths for tissue imaging, in particular second (1,100 nm to 1,350 nm), third (1,600 nm to 1,870 nm) and fourth centered about 2200 nm optical windows, for example, arteries, bones, teeth, brain and breast. At these wavelengths tissue becomes more transparent and clearer due to much less scattering of light. Optical attenuation from normal and malignant breast and prostate tissues, and pig brain in the spectral range of 400 to 2,500 nm was measured to show deeper penetration distances. With these NIR optical windows and an InGaAs and InSb camera detector, optical images of chicken tissue overlying black wires were also obtained. The most effective measure in the reduction of mortality and morbidity from cancer and other disease conditions is detection at an early stage of disease by X-ray mammography. The use of these longer NIR wavelengths with new 2D photodetectors and high speed computers may allow for better imaging techniques in areas other than X-ray mammography such as NIR optical mammography and carotid artery imaging for plaques, imaging bone cracks, and imaging internal structure of teeth, root canal.

1.1 Imaging Through Tissue Media

Light through turbid media can be described by the trajectories (diffusive, ballistic and snake) of photons [10]. With increasing propagation distance, these photons will be attenuated by the effects of scattering and absorption and cause a reduction in image quality. Absorption of light in tissue media can occur by select biomolecules such as collagen and elastin, by lipids, by hemoglobin, and by water molecules in tissue media, while scattering can occur by cells, cell nuclei and organelles. Water molecules, in particular, greatly affect image quality and penetration depth due to strong absorption peaks from vibrational modes at ~900 nm, ~1,200 nm, ~1,400 nm and ~1,900 nm. These effects can be minimized and produce clearer optical images of tissue by using thin tissue slices (less than 1 mm) and by allowing the ballistic photons (described by Lambert-Beer's intensity law) to govern over the diffusive photons. These photons can be measured by the total attenuation coefficient ($\mu_t$), where $\mu_t$ is the inverse of the total length traveled by the ballistic photons in the tissue media (known as the total attenuation length ($l_t$) and is determined by combining the absorption ($\mu_a$) and scattering ($\mu_s$) coefficients ($\mu_t = \mu_a + \mu_s$).

Figure 1:
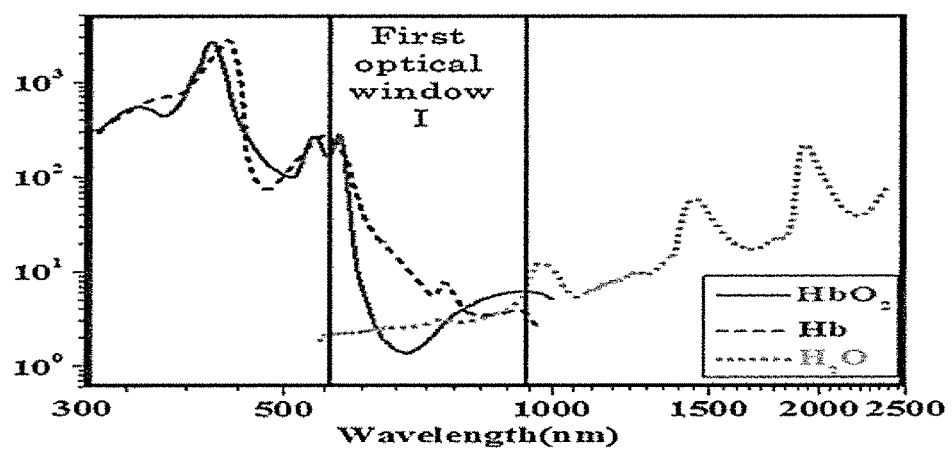
FIG. 1 shows absorption spectra of deoxyhemoglobin (Hb), hemoglobin (HbO$_2$), water in the visible and NIR regions from 400 nm to 2500 nm.

In the first region of minimal water absorption between water peak maxima (first NIR optical window from 650 nm to 950 nm), images are blurred due to strong absorption peaks from lipids, from hemoglobin and deoxy-hemoglobin, and due to the molecular process of Rayleigh/Mie scattering. FIG. 1 highlights the absorption properties of deoxyhemoglobin (Hb), hemoglobin ($HbO_2$), and water ($H_2O$) in the first optical window [4]. FIGS. 2(a)-2(c) show the absorption spectra of lipids and collagen for wavelengths from combination vibrational modes for >1500 nm.

1.2 Second and Third Optical Windows

Recently, a new NIR wavelength transmission window from 1,100 nm to 1,350 nm located between two additional water peaks has been used for in vivo imaging. Limited studies on this second optical window have been reported due to strong water absorption and lack of 2D NIR photodetectors. Today, with advances in the spectral response of NIR charge-coupled device (CCD) image sensors have made NIR camera specificity possible up to a wavelength of 2,200 nm. As a result, longer wavelengths can be used, in particular, at a new third NIR spectral region from 1,600 nm to 1,870 nm, between two strong water peaks (1444 am and 1950 nm), to image deeper into tissue media. This region had been previously ignored due to water absorption. A small amount of absorption can help minimize the detection of diffusive photons, which cause images to blur, and highlight the ballistic and snake photons which are responsible for producing clearer images. The tissue becomes more glass-like in the second and third spectral window and is having less blurring effect and clearer images.

2. Experimental

Optical attenuation measurements and optical images from tissue in the second and third NIR spectral windows (1,100 nm to 1.350 nm and 1,600 nm to 1,870 nm, respectively) were obtained and compared with the first NIR spectral window. Optical images using the fourth optical window were not investigated due to lack of detector sensitivity. Normal and malignant human breast and prostate tissues were supplied by the National Disease Research Interchange (NDRI) and the Cooperative Human Tissue Network (CHTN) under an institutional review board (IRB) protocol. The tissue samples were not fixed or chemically treated. The pig brain sample was not frozen prior and measurements were performed within 24 hours of resection. All other samples were kept in a low temperature freezer (minus 80° C.) to preserve freshness. Prior to the spectroscopic studies, the tissues samples were removed from the freezer and allowed to reach room temperature. Any excess water moister was removed before performing the measurements.

2.1 Optical Attenuation

Optical attenuation measurements from normal and malignant human breast and prostate tissues, and pig brain were obtained at each of the three optical windows. Breast and prostate tissue samples were cut to a thickness of ~50 μm, 100 μm, and 200 μm and placed in thin quartz cuvettes. Pig brain tissue was cut to a thin thickness of ~100 μm. Thin tissue slices were necessary for ballistic light to dominate over diffusive light. The optical density spectra from the tissue slices were obtained using a Perkin-Elmer Lambda UV/VIS/NIR Spectrophotometer in the spectral range of 400 nm to 2,500 nm.

2.2 Imaging Using the Second and Third Optical Windows

Transmission images (322×224 pixels) of chicken breast tissue with black wires of various thicknesses were obtained using the second and third NIR windows and the optical setup in FIG. 2. Chicken tissues were sliced to thicknesses of 1.6 mm, 2.8 mm, 3.9 mm and 7.4 mm and placed on top of the three wires. The depths of the wires were measured as 0.75 mm (left of image), 0.95 mm (center) and 1.35 mm (right).

Figure 3:
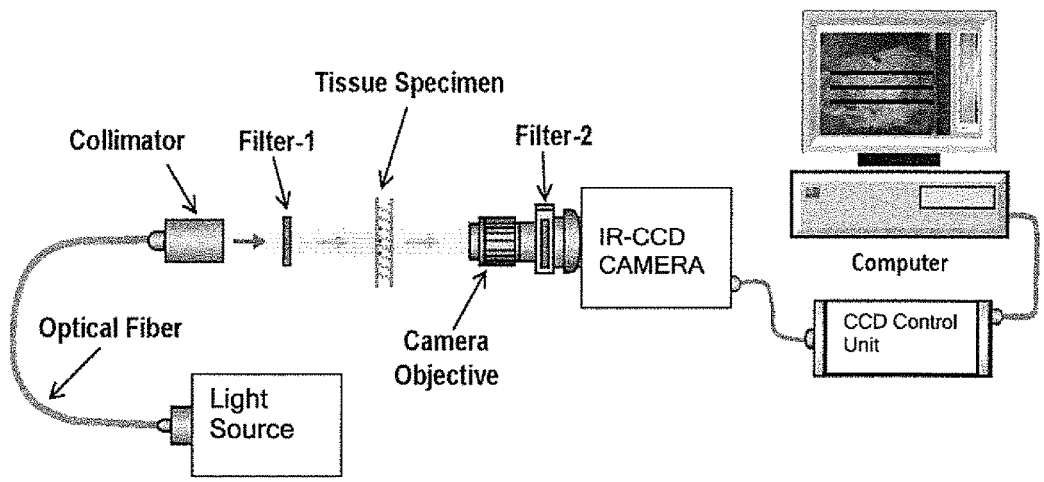
FIG. 3 illustrates a setup for optical imaging of tissue specimen using the second and third optical windows with and without xyz scanner.

The optical setup (seen in FIG. 3) includes a halogen lamp light source with spectral distribution from 200 nm to 2,500 nm, selective filters at 1,120 nm HW 40 and at 1,500 nm longpass for the second and third optical window, respectively, and an IR-CCD InGaAs camera (Goodrich Sensors Inc. high response camera SU320KTSW-1.7RT) with spectral response between 0.9 μm and 1.7 μm (highlighting the second and third optical window). The 1,500 nm longpass filter was used to cutoff light of wavelengths below 1,500 nm. This allowed for the transmission of light from the third window with wavelengths up to 1,700 nm. The absorption in spectral windows 2 and 3 is due to absorption by lipids, collagen, and water in tissue. The absorption by lipids, collagen, and water are due to combination vibrational modes. One would use windows 2 and 3 to detect lipids and collagen in arteries in neck (carotid arteries).

Figure 4:
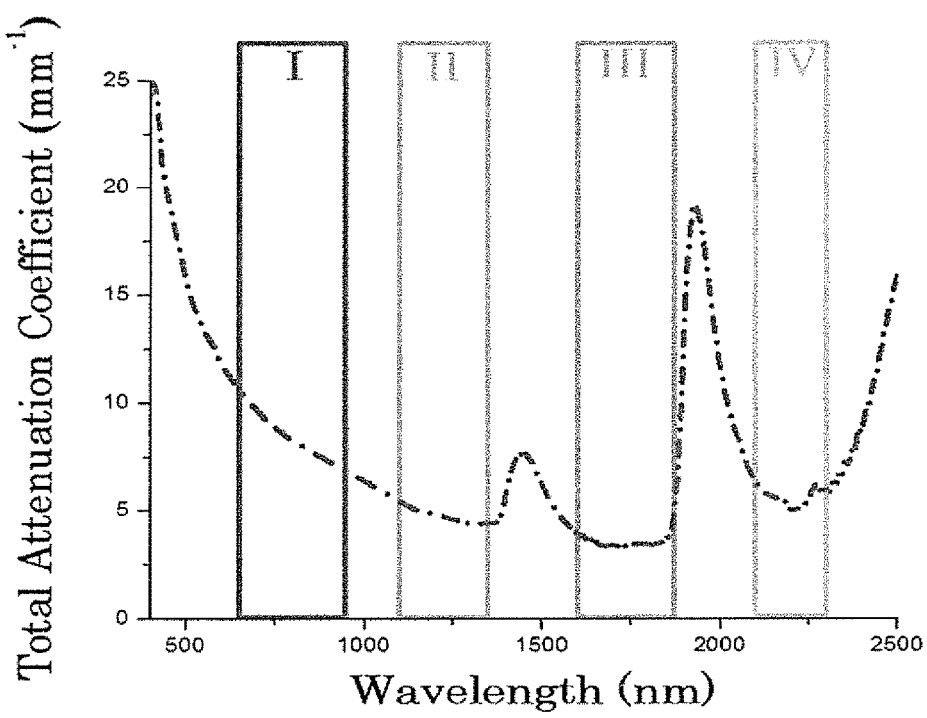
FIG. 4 illustrates a spectrum of the total attenuation coefficient ($\mu_t$) from normal prostate tissue using the I, II, III, and a possible IV optical windows.

3. Results and Discussion 3.1 Optical Attenuation Spectra of Human Prostate Tissue, Human Breast Tissue, and Pig Brain FIG. 4 shows the spectrum of total attenuation coefficient ($\mu_t$) in mm from thin prostate tissue with a depth of 200 μm in the spectral range of 400 nm to 2,500 nm with three optical windows highlighted. $\mu_t$ is defined by combining the absorption ($\mu_a$) and scattering ($\mu_s$) coefficients (where $\mu_t$ is equal to $\mu_a+\mu_s$). The ballistic light in the thin tissue media depends on $\mu_a$ plus $\mu_s$. The total attenuation coefficient ($\mu_t$) was calculated from the transmission spectrum of the tissue using the equation $\mu_t$ equals 2.303 times the transmission data divided by the depth of the tissue sample z (thin tissue thickness of 200 microns) derived from Lambert-Seer's equation $I/I_o=\exp[-(\mu_t z)]$. Also noted is a fourth (IV) optical window centered at 2,200 nm which could be of interest for imaging.

Figure 5:
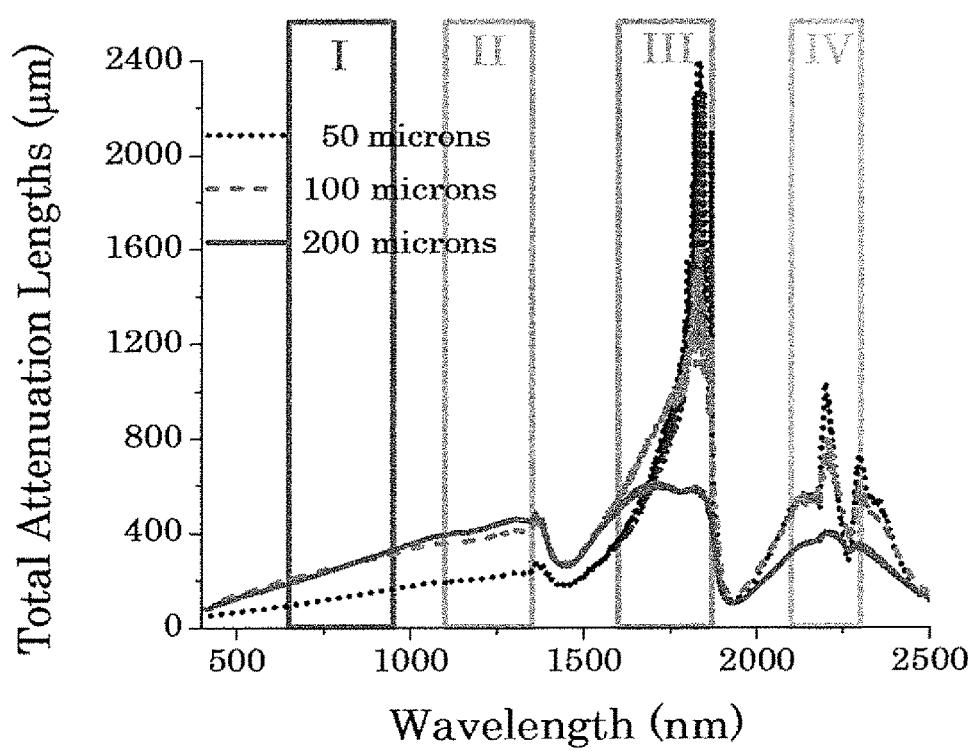
FIG. 5 illustrates a spectrum of the total attenuation lengths ($l_t$) in um from normal prostate tissue at different depths of 50, 100 and 200 microns using the I, II, III, and IV optical windows.

FIG. 5 shows the corresponding spectrum of the total attenuation length ($l_t$) in μm from normal prostate tissue with depths of 50, 100 and 200 micrometers, where $l_t^{-1}$ or the total attenuation coefficient ($\mu_t$), in the spectral range of 400 nm to 2,500 nm. $l_t$ is noticeably largest in the third optical window with a peak maximum at 1,835 nm.

Figure 6:
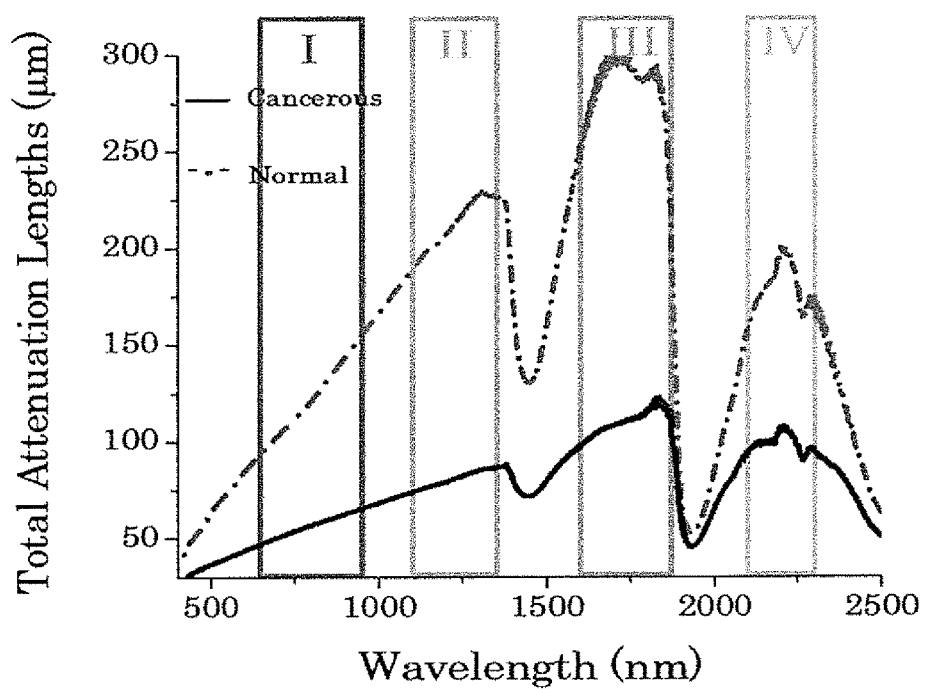
FIG. 6 illustrates a spectrum of the total attenuation lengths ($l_t$) in μm from normal and cancerous prostate tissues using the I, II, III, and IV optical windows.
Figure 7:
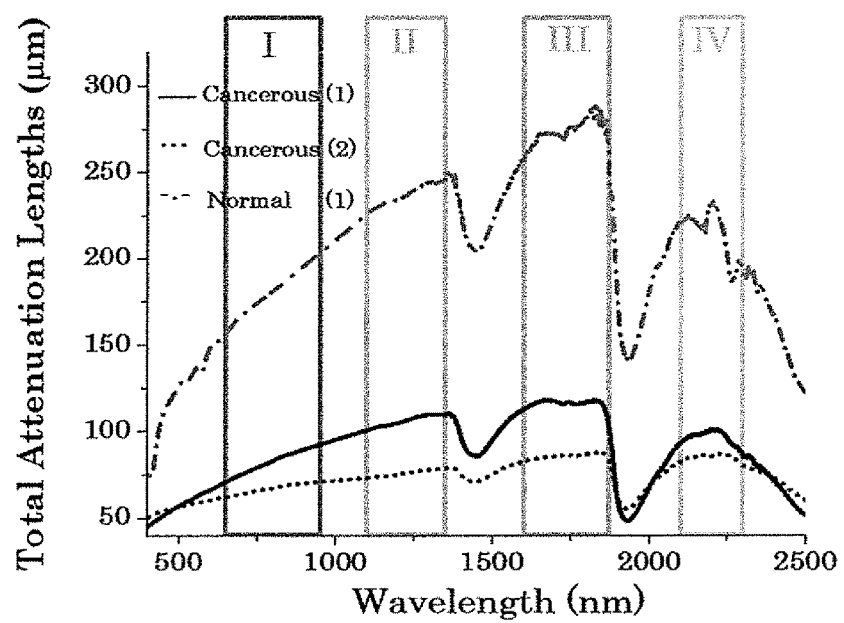
FIG. 7 illustrates a spectrum of the total attenuation length (lt) in μm from normal and cancerous breast tissues from two patients using the I, II, III, and IV optical windows.

FIGS. 6 and 7 show the total attenuation lengths ($l_t$) in μm from normal and malignant prostate and breast tissues with a depth of 200 μm. A larger total attenuation length ($l_t$) occurs in the new third optical window compared to the first, second and the possible fourth optical windows. We also notice that $l_t$ from normal tissue is larger compared to the malignant tissue samples.

Table 1. Optical properties $l_t$ (μm) from tissues in the three (I, II, III) and possible fourth (IV) optical windows from wavelengths at 750, 1,200, 1,700 and 2,200 nm.

TABLE 1

Optical properties $l_t$(μm)from tissues in the
three(I, II, III) and possible fourth(IV) optical windows
from wavelengths at 750, 1,200, 1,700 and 2,200 nm

| Tissue Details | | Total Attenuation Lengths $l_t$ (μm) | | | |
|---|---|---|---|---|---|
| Depth (μm) | Type | I | II | III | IV |
| 50 | Prostate Normal | 120 | 207 | 611 | 1038 |
| 100 | Prostate Normal | 245 | 373 | 818 | 731 |
| 200 | Prostate Normal | 207 | 414 | 589 | 401 |
| 100 | Prostate Cancer | 161 | 168 | 206 | 209 |
| 200 | Prostate Cancer | 101 | 159 | 217 | 213 |
| 50 | Breast Normal (1) | 130 | 174 | 250 | 270 |
| 100 | Breast Normal (1) | 209 | 242 | 300 | 319 |
| 200 | Breast Normal (1) | 167 | 234 | 271 | 232 |
| 100 | Breast Cancer (1) | 169 | 311 | 438 | 365 |
| 200 | Breast Cancer (1) | 66 | 75 | 86 | 86 |
| 50 | Breast Cancer (2) | 23 | 30 | 33 | 33 |
| 100 | Breast Cancer (2) | 66 | 99 | 127 | 132 |
| 200 | Breast Cancer (2) | 79 | 105 | 117 | 101 |
| 100 | Pig Brain | 190 | 235 | 279 | 291 |

Table 1 summarizes the results obtained from the total attenuation lengths ($l_t$) of normal and cancerous breast and prostate tissue, and pig brain at select wavelengths representing the four optical windows. $l_t$ were measured at wavelengths of 750 nm, 1,200 nm, 1,700 nm, and 2,200 nm. Wavelengths of 1,200 nm and 1,700 nm were chosen to correspond to wavelengths in the second and third optical windows and used in the optical setup to acquire images of chicken tissue in the detector range up to 1,700 nm.

As the wavelength is increased, $\mu_s$ is reduced and $\mu_a$ dominates. A reduction in $l_t$ can be seen in the fourth optical window, at wavelengths greater than 1,900 nm, due to a combination of vibrational modes from lipids, collagen, and water molecules in the tissues (and is illustrated by the FIGS. 4-7). Tis region can be used to detect veins, arteries, and flow of blood. The maximum penetration depth ($l_t$) occurred in the third optical window around 1,835 nm for all tissue samples. Normal prostate tissue with a depth of 100 μm had a penetration depth of ~800 μm at a wavelength of 1,700 nm using the third optical window.

3.2 Images of Chicken Tissue and Wires at Different Depths

Figure 8A:
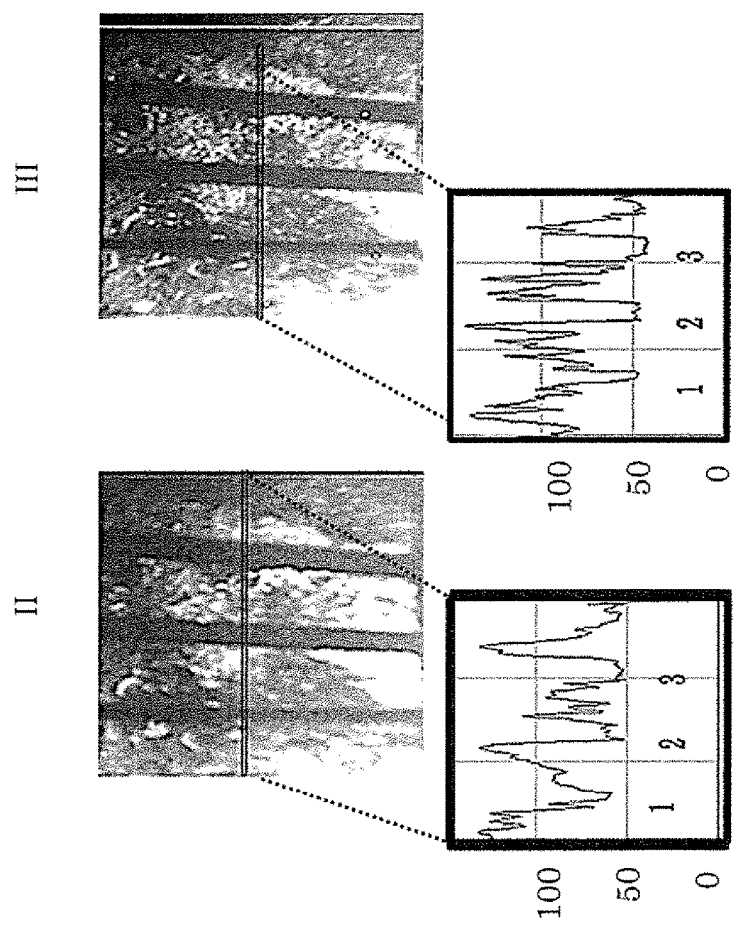
Figure 8B:
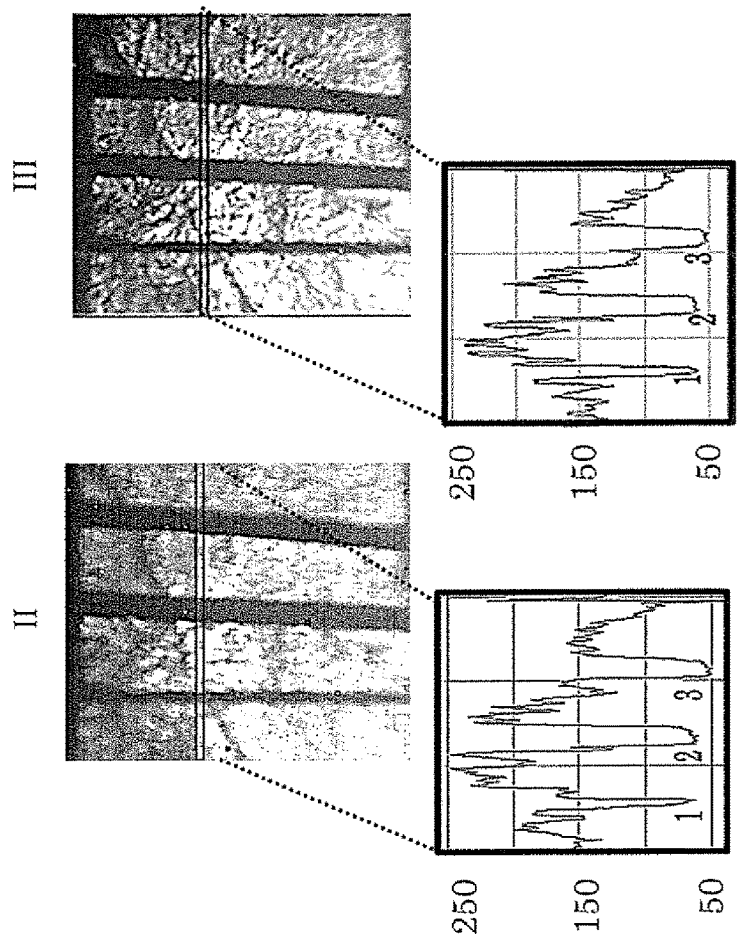

FIG. 8 Transmission images, seen in FIG. 8 and acquired using the optical setup in FIG. 2, illustrate the appearance of the black wires (0.75 mm (left), 0.95 mm (middle) and 1.35 mm (right)) through tissue slices (ranging from no top tissue layer, to a layer of 3.9 mm thick with a bottom layer of 1.8 mm). Light from wavelengths in the second and third windows was able to penetration the thick tissue layer and give clear images of the hidden wires. Images of the three wires with an overlaying layer of 1.6 mm tissue have the highest contrast percentage while the images of the wires with an overlaying layer of 3.9 mm tissue are slightly blurred but still visible. The images using the second and third optical windows at the 7.4 mm thickness (not shown) over wires were apparent on the screen during the experimental procedure and before the imaging process. Using this optical setup, images of the three wires were recorded with a transmission maximum penetration depth of 3.9 mm.

Penetration depth analysis was done on the images of the three (1, 2, 3) wires through chicken breast tissue at the second and third optical windows. The corresponding digitized spatial intensity distributions of the images were obtained by integrating the image intensity over the horizontal rectangular region (as marked by a black box). A plot of intensity versus pixels of the wires and chicken breast tissue in the second and third windows is also shown in FIG. 8.

The image intensity can be described by the light intensity transmitted through the chicken breast tissue onto the three wires. From FIG. 8, the second and third optical windows have minimal noise and clear images through tissue media.

TABLE 2

Contrast results from the images of the three wires
and chicken breast tissue of various depths.

| Tissue Thickness (mm) | $2^{nd}$ Window | $3^{rd}$ Window |
|---|---|---|
| No tissue | 67.8% | 76.4% |
| 1.6 | 75.2% | 76.2% |
| 2.8 | 58.5% | 43.1% |
| 3.9 | 32.1% | 24.0% |

Table 2 summarizes the contrast results from images of chicken tissue of different depths and three wires using the second and three optical windows. The degree of contrast can be calculated as the intensity of signal minus intensity of background divided by intensity of signal plus intensity of background times 100%. The third and second optical windows have similar signal to background ratios.

Due to a reduction in scattering in tissue media at longer NIR wavelengths, longer attenuation and clearer images can be seen in the second and third NIR windows and provides additional information to that observed using the conventional first NIR window. Deeper NIR images can be achieved due to a reduction in the scattering coefficient, allowing the absorption coefficient to be the main determinant of image quality for arteries for plaques and lipids. Optimizing tissue image contrast from the NIR second and third windows is needed. Better NIR light source such as intense tunable lasers Forestrite (1,150 nm-1,300 nm), Cunyite (1,200 nm-1,500 nm and LSO (1,110 nm-1,600 nm), Ti sapphire 700 nm to 1100 nm and the Supercontinuum laser source (400 nm-2,500 nm), or semiconductor laser diodes will eliminate photon starvation and improve sensitivity and signal to noise ratio. Using a more intense NIR light source in optical mammography, could provide deeper depth penetration and better optical images of abnormalities which are hidden behind normal tissue. Imaging through fog, or cloudy water, for example, may also benefit. New microscopes use laser source, xy z scanner, NIR photon detectors and imager such as InGaAs and InSb and others coupled to computer for display of 1 Photon and multiphoton (2PEF, SHG).

While the invention has been shown and described with reference to certain embodiments thereof, it will be understood by those skilled in the art that various changes in form and detail may be made therein without departing from the spirit and scope of the invention as defined by the appended claims and their equivalents.

The invention claimed is:

1. Apparatus for deep optical imaging of tissue comprises a coherent light source with spectral distribution from about 400 nm to 2500 nm; a first bandpass light filter and a second bandpass light filter spaced from said first light filter, said first and second filters being selected to have substantially similar filtering properties for passing optical frequencies within one of a second, third and fourth near-infrared spectral window for deep optical imaging of tissue in the selected window; means for placing a tissue sample between said first and second light filters; an IR-CCD camera for receiving light after it passes through said first light filter and the tissue sample and emerges from said second light filter and having a spectral response within the approximate range of 0.9 μm-2.4 μm, whereby selected molecules or cells within one of the optical windows can be highlighted and the tissue imaged in one of the following windows: window 2 at 1100 nm-1350 nm, window 3 at 1600 nm-1800 nm and window 4 at 2200 nm-2400 nm with reduced scattering and improved signal-to-noise to provide clearer images inside tissue for microscopes for linear and non linear processes.

2. An apparatus as defined in claim 1, wherein said first and second filters have bandwidths no greater than approximately 250 nm.

3. An apparatus as defined in claim 1, wherein tissues to be imaged include one or more collagen, elastin, lipids and other biomolecules from vibrational modes from the group comprising the brain, arteries, prostate, mouth, colon, breast, intestines, skin, bones and veins using NIR in four windows with xyz imaging.

4. An apparatus as defined in claim 1, wherein plaques and fats in carotid arteries and veins are detected.

5. An apparatus as defined in claim 1, wherein bone fractures and cracks from collagen are detected.

6. An apparatus as defined in claim 1, wherein dental decay in teeth is detected.

7. An apparatus as defined in claim 1, wherein roots in teeth are detected for root canal.

8. An apparatus as defined in claim 1, wherein NIR from 900 nm to 3000 nm is used to image in tissues.

9. An apparatus as defined in claim 1, wherein the apparatus is used for imaging backscattering geometry.

10. An apparatus as defined in claim 1, wherein the apparatus is used for imaging forward transmission geometry.

11. An apparatus as defined in claim 1, wherein the apparatus uses NIR windows for microscope imaging in tissues and vessels and cells.

12. An apparatus as defined in claim 1, wherein said coherent light source is selected from the group consisting of the following NIR lasers providing the laser beams from: semicondutor, TiI sapphire, supercontinuum, rare earth doped solid state lasers, OPO, Y or Er fibers, optical fiber lasers in 1000 nm to 2000 nm.

13. An apparatus as defined in claim 1, wherein said IR-CCD camera comprises at least one of an InGaAs and an InSb camera.

14. An apparatus as defined in claim 1, further comprising a collimator for collimating the light from said light source prior to passing the light through said light filter.

15. An apparatus as defined in claim 1, where cancer can be detected using changes in collagen and Lipid NIR absorption in the NIR windows selected.

16. A method of deep imaging of tissue comprising the steps of providing a coherent light source arranged to transmit light through a tissue sample or specimen to be imaged, said light source having a spectral distribution from 400 nm to 2500 nm; filtering with a first bandpass filter the light generated by said light source prior to passing the light through the tissue sample; filtering with a second bandpass filter light following passage through the tissue sample, said first and second filters being selected to have substantially similar filtering properties for passing optical frequencies within one of a second, third and fourth near-infrared spectral windows for deep optical imaging of tissue in the selected window; imaging the light emanating from the second filter having a spectral response within the approximate range of 0.9 μm-2.4 μm; and selectively displaying one of the second, third and fourth optical windows for deep optical imaging of the tissue sample with reduced scattering and improved signal-to-noise.

17. An method as defined in claim 16, where cancer can be detected using changes in collagen and Lipid NIR absorption in the NIR windows selected.

* * * * *